(12) United States Patent
Jamiolkowski et al.

(10) Patent No.: US 6,206,897 B1
(45) Date of Patent: Mar. 27, 2001

(54) ENHANCED VISUALIZATION OF THE LATCHING MECHANISM OF LATCHING SURGICAL DEVICES

(75) Inventors: Dennis D. Jamiolkowski, Long Valley; Leslie Hamilton, Ringoes, both of NJ (US); Richard Smith, Loveland, OH (US); Robert F. Bencini, Sunnyvale, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 08/348,699

(22) Filed: Dec. 2, 1994

(51) Int. Cl.[7] .................. A61B 17/064; A61B 17/122
(52) U.S. Cl. .................. 606/157; 606/158; 606/220
(58) Field of Search .................. 606/219–221, 606/151, 157, 158; 227/902

(56) References Cited

U.S. PATENT DOCUMENTS

| D. 280,931 | 10/1985 | Green | D24/26 |
|---|---|---|---|
| D. 280,932 | 10/1985 | Green | D24/27 |
| 3,625,352 | * 12/1971 | Perkins | 206/56 DF |
| 3,949,755 | 4/1976 | Vauquois . | |
| 4,008,303 | * 2/1977 | Glick et al. | 264/210 F |
| 4,052,988 | 10/1977 | Doddi et al. . | |
| 4,402,445 | * 9/1983 | Green | 227/19 |
| 4,506,670 | 3/1985 | Crossley . | |
| 4,513,746 | 4/1985 | Aranyi et al. . | |
| 4,523,591 | * 6/1985 | Kaplan et al. | 606/220 |
| 4,534,350 | * 8/1985 | Goldon et al. | 606/220 |
| 4,534,352 | * 8/1985 | Korthoff | 606/220 |
| 4,610,250 | 9/1986 | Green . | |
| 4,667,674 | 5/1987 | Korthoff et al. . | |
| 4,805,617 | 2/1989 | Bedi et al. . | |
| 4,932,960 | 6/1990 | Green et al. | 606/220 |
| 4,972,949 | 11/1990 | Peiffer . | |
| 5,057,118 | 10/1991 | Picha . | |
| 5,089,009 | 2/1992 | Green | 606/219 |
| 5,358,510 | 10/1994 | Luscombe et al. | 606/220 |

FOREIGN PATENT DOCUMENTS

| 0 490 411 A1 | 12/1991 | (EP) . | |
| 0 592 000 A2 | 10/1993 | (EP) . | |
| 0 609 612 A2 | 10/1994 | (EP) | A61B/17/12 |

OTHER PUBLICATIONS

Premium Curved EEA, Disposable Circulair Hechtinstrument (Apr. 4, 1989); Auto Suture Benelux.

* cited by examiner

Primary Examiner—Michael H. Thaler

(57) ABSTRACT

A surgical device having a latching mechanism comprising a latch member; and a retaining member having at least one aperture adapted to receive and retain said latch member in a locked position, said latch member and said retaining member being of contrasting colors so that when the latch member is locked in place by the retaining member that the latch member's presence in the locked position is externally visible.

10 Claims, 3 Drawing Sheets

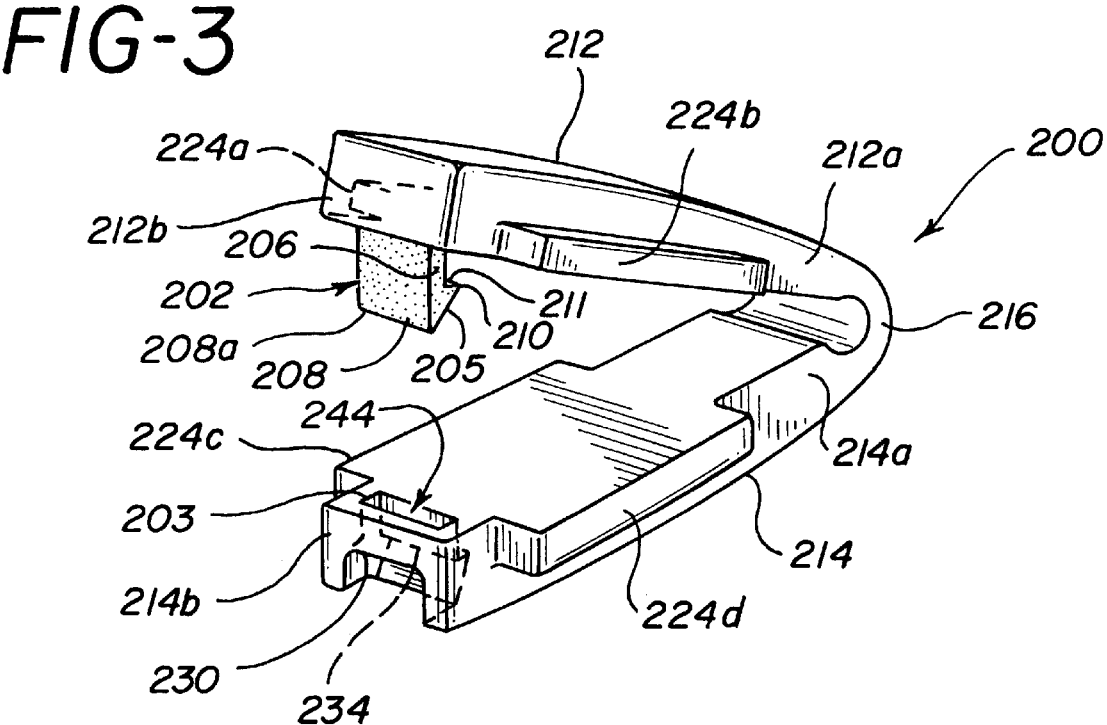
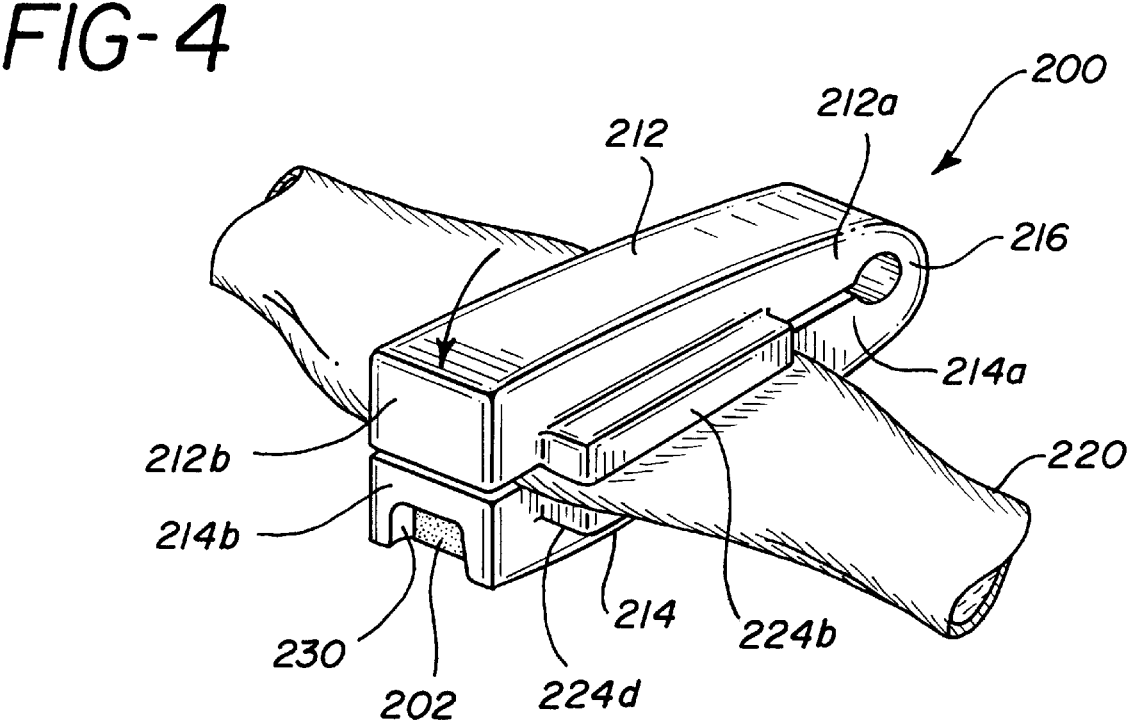

ENHANCED VISUALIZATION OF THE LATCHING MECHANISM OF LATCHING SURGICAL DEVICES

FIELD OF THE INVENTION

The field of art to which this invention relates is surgical implements and more specifically, to the surgical devices with latching mechanisms, such as surgical staples and receivers, ligating clips and the like.

BACKGROUND OF THE INVENTION

Surgical devices of one and two part construction are quite well-known in the art. Examples of surgical devices such as surgical fasteners are described in U.S. Pat. Nos. 4,402,445, 4,506,670, 4,513,746, 4,534,352, 4,610,250, 4,667,674 and 4,932,960, all of which are incorporated herein by reference. Typically, these surgical devices contain two members formed from one or more absorbable materials. The device generally consists of at least one latching member i.e. a staple or fastener, and a retaining member. The latching member generally pierces the tissue in one or more locations and is locked into the retaining member.

In surgery, the surgical personnel who applies the surgical device using a mechanical applier often has no easy way to determine whether the latching member has locked into the retaining member. Currently, surgical personnel must manipulating the tissue to check for loose or unsecured staples, which is a time consuming procedure. Additionally, manipulating the tissue in this procedure leads to more tissue trauma and increases the risk of postoperative infections. What is needed, then, are surgical devices that permit surgical personnel to quickly determine whether a surgical device is secured.

Accordingly, it is an object of the present invention to provide a surgical device that permits surgical personnel to easily determine whether the surgical device is secured, thereby reducing the time required for surgical procedures. It is another object of the present invention to provide a surgical device that reduces the amount of tissue manipulation occurring during surgical procedures, thereby decreasing tissue trauma and the risk of postoperative infections. This and other objects and advantages will be apparent to those skilled in the art from the foregoing description of the present invention.

SUMMARY OF THE INVENTION

We have discovered a surgical device having a latching mechanism comprising a latching member; and a retaining member having at least one aperture adapted to receive and retain said latching member in a locked position; said latch member and retaining member being of contrasting colors so that when the latch member is locked in place by the retaining member that the latch member's presence in the locked position is visible.

DESCRIPTION OF THE DRAWINGS

FIG. 3 is a perspective view of a ligating clip.

FIG. 4 is a perspective view of the ligating clip of FIG. 3 secured to a vessel.

DETAILED DESCRIPTION OF THE INVENTION

Figure 1:
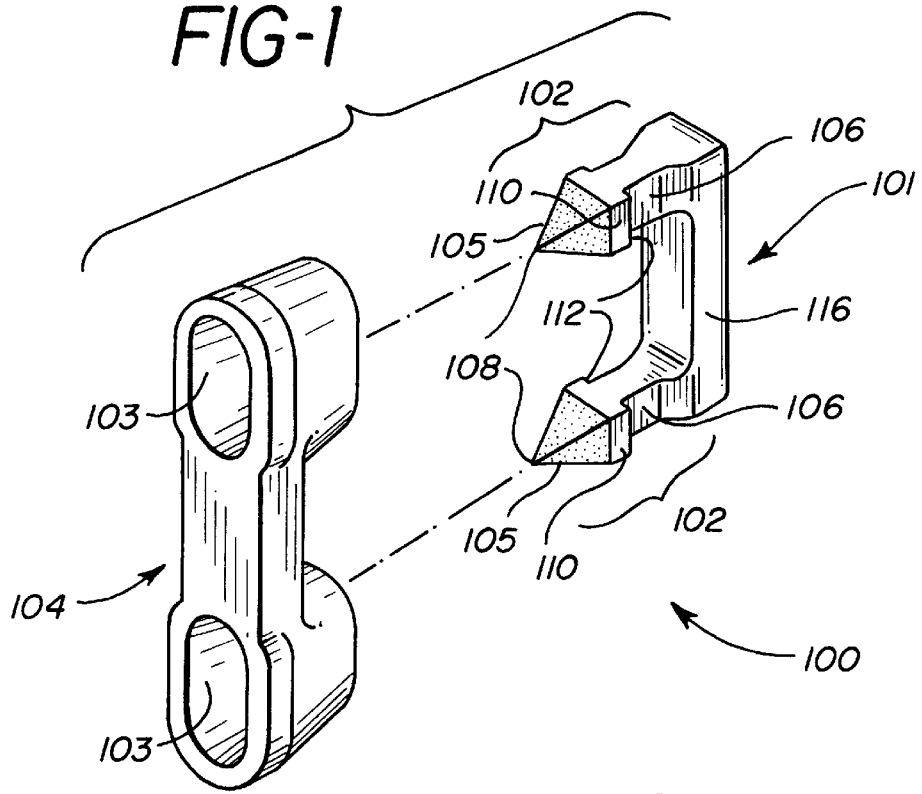
FIG. 1 is a perspective of the latch member and retaining member.
Figure 2:
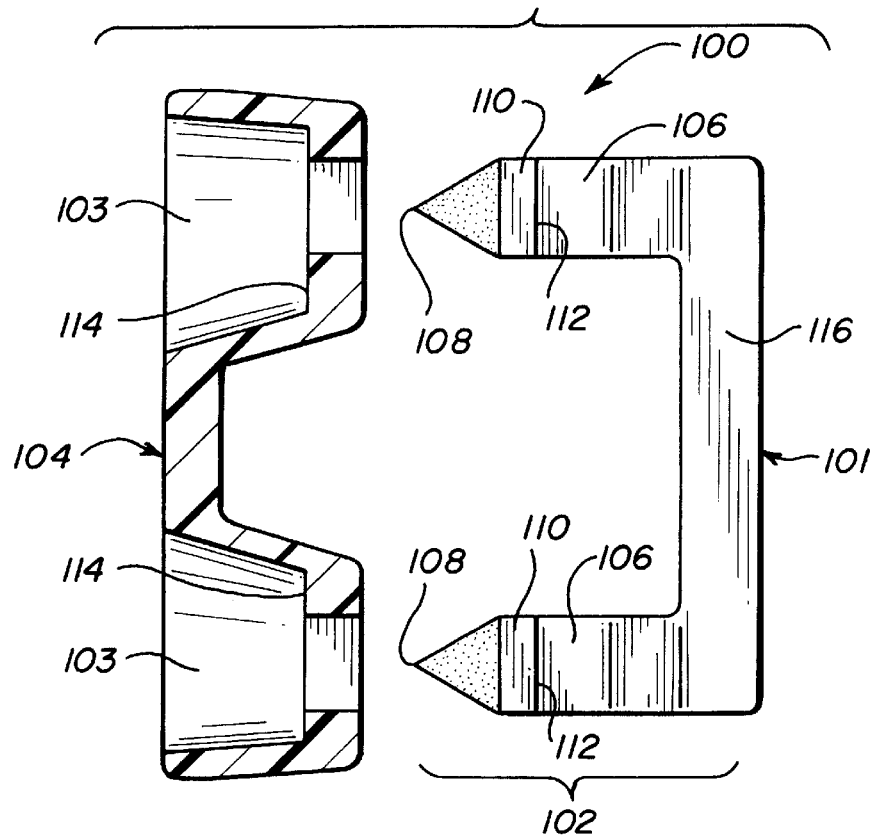
FIG. 2 is a cross-sectional view of the latch member and the retaining member of FIG. 1.

The inventive surgical latching device of polymeric material is shown in FIG. 1, FIG. 2, FIG. 3 and FIG. 4. The latching device shown in FIG. 1 and FIG. 2 comprises a retaining member 104 and latching member 101, which has a base 116 and at least two latches 102. The latches 102 are substantially parallel and extend substantially perpendicularly from the same side of the base 116. The latches 102 are generally attached to the base 116 adjacent to the ends of the base 116. If more than two latches are placed on the base 116, then the latches are spaced along the length of the base 116. The latches 102 have barbs 105 which attach to shank 106. The barbs 105 are tapered from the bottom 110 to the tip 108 of the barb 105 on at least on one side of the barb 105. The bottom 110 of the barb 105 is wider than the shank 106. The bottom 110 of the barb is joined to the shank 106. An interlocking barb surface 112 is provided adjacent to the junction of the bottom 110 of the barb 105 and the shank 106.

In surgical application the tissue to be joined is positioned between retaining member 104 and latching member 101. The two latches 102 of latching member 101 are driven through tissue (not shown) into aperture 103 in the retaining member 104. The latches 102 deflect as they pass through apertures 103, but substantially return to their original orientation when the interlocking barb surface 112 overlaps and engages locking surface 114. The engagement of the interlocking barb surface 112 of the latching member 101 and the locking surface 114 of retaining member 104 fastens the two members together with the tissue sandwiched in place between the two members 101 and 104, in the locked position.

FIG. 3 and FIG. 4. illustrate a ligating clip, which is a second embodiment of the present invention. The ligating clip 200 includes a latching member 212 and retaining member 214 connected at their proximal ends 212a and 214a by a resilient hinge section 216. Provided at the distal ends 212b and 214b of the latching and retaining members 212 and 214 is a latching mechanism 218 for locking the members 212 and 214 in a closed position about body tissue, such as a vessel 220, shown in FIG. 4. In the illustrated embodiment, the latch mechanism is comprised of a latch 202 which is adapted to be lockingly received within a retainer 244 located in the distal end of 214b of the retaining member 214. The latch 202 is comprises a barb 205 which is attached to shank 206. The tip 208 is provided with a sharp edge 208a for penetrating any tissue (not shown) which might surround the vessel 220. The barb 205 is flared from the tip 208 to the bottom 210. The bottom of the barb 210 is wider that the shank 206. The bottom 210 of the barb is joined to the shank 206. An interlocking barb surface 211 is provided adjacent to the junction of the bottom 210 of the barb 205 and the shank 206. The retainer 244 has an aperture 203 adapted to receive the latch 202 and a locking surface 234 adapted to engage interlocking barb surface 211 to maintained the ligating clip in the closed or locked position. Inspection port 230 at the distal end of retaining member 214 provides a means for visually inspect whether the latch 202 is locked into retainer 244.

First and second lateral extensions 224a and 224b are integrally formed with the latching member 212, and the third and fourth lateral extensions 224c and 224d extend outwardly from opposing wide walls of the retaining members 214 and are adapted to receive a clip closing force. The force applied to lateral extensions 224a–224d cause the distal ends 212b and 214b of the members 212 and 214 to move towards one another. The tip 208 of latching member 202 is driven through tissue (not shown) into aperture 203 in the retainer 244. The latch 202 deflect as it passes through aperture 203 but substantially returns to its original orientation when the interlocking barb surface 211 overlaps and engages locking surface 234. The engagement of the interlocking barb surface 211 of the latching member 202 and the locking surface 234 of retaining member 244 fastens the two members together with the tissue sandwiched in place between the two members 212 and 214, in the locked position, with the vessel 220 engaged therebetween as shown in FIG. 4.

To facilitate allowing surgical personnel to determine whether the surgical latching device in the locked position, a portion of the latch i.e. barbs (105, 205) as compared to a portion of the retainer i.e. locking surface (114, 234) and/or the apertures (103, 203) should be of contrasting colors. The entire latching member (101, 212) may also be of a contrasting color to enhance the visibility of the latching member being locked into retaining member (104, 214). As illustrated in FIG. 4 the inspection port 230 is provided to allow for visual inspection of the ligating clip to verify the clip is in the locked position. The inspection port may consist of an opening or a substantially transparent view port.

The contrasting colors preferably will show up easily against a film of blood, and most preferably one of the colors will appear dark and one color appears light. The contrasting colors can be created by using a colorant such as a dye or pigment. The colorant can be added to the polymeric material used to make the latching member or the retaining member. The colorant can also be added as an external coating. Suitable colorants are listed in the *Handbook of U.S. Colorants for Foods, Drugs, and Cosmetics,* second edition by Daniel M. Marmion which is hereby incorporated by reference. Colorants commonly used include D&C Violet No.2, D&C Green No.6, D&C Green No.5, D&C Blue No.6, [phthalocyaninato] (2-)] copper and black logwood dye. Additionally, when polymeric materials are used to form the surgical devices the contrasting colors can be created by leaving one component its natural color, "undyed" (i.e. white to golden color) and coloring the other component with an appropriate contrasting colorant. Currently preferred contrasting colors include but are not limited to contrasting colors selected from the group consisting of undyed/green, undyed/violet, undyed/blue, undyed/black, green/black, green/violet, green/blue and blue/black.

The surgical devices of the present invention can be made from biocompatable metals or polymeric materials which may or may not be bioabsorbable. Preferred absorbable polymers include poly(p-dioxanone), poly(glycolide), poly(lactide), poly(caprolactone), poly(hydroxybutyrate), poly(hydroxyvalerate), poly(anhydrides), copolymers thereof and blends thereof. Preferred non-absorbable polymers include nylon, polyester and polypropylene. The surgical devices may be molded or machined from these biocompatable materials.

The surgical devices of the present invention can be applied with many mechanical appliers such as the applier described in European Patent Application 93308924.5 (Publication No. 609612), which is hereby incorporated by reference herein.

Figure 5:
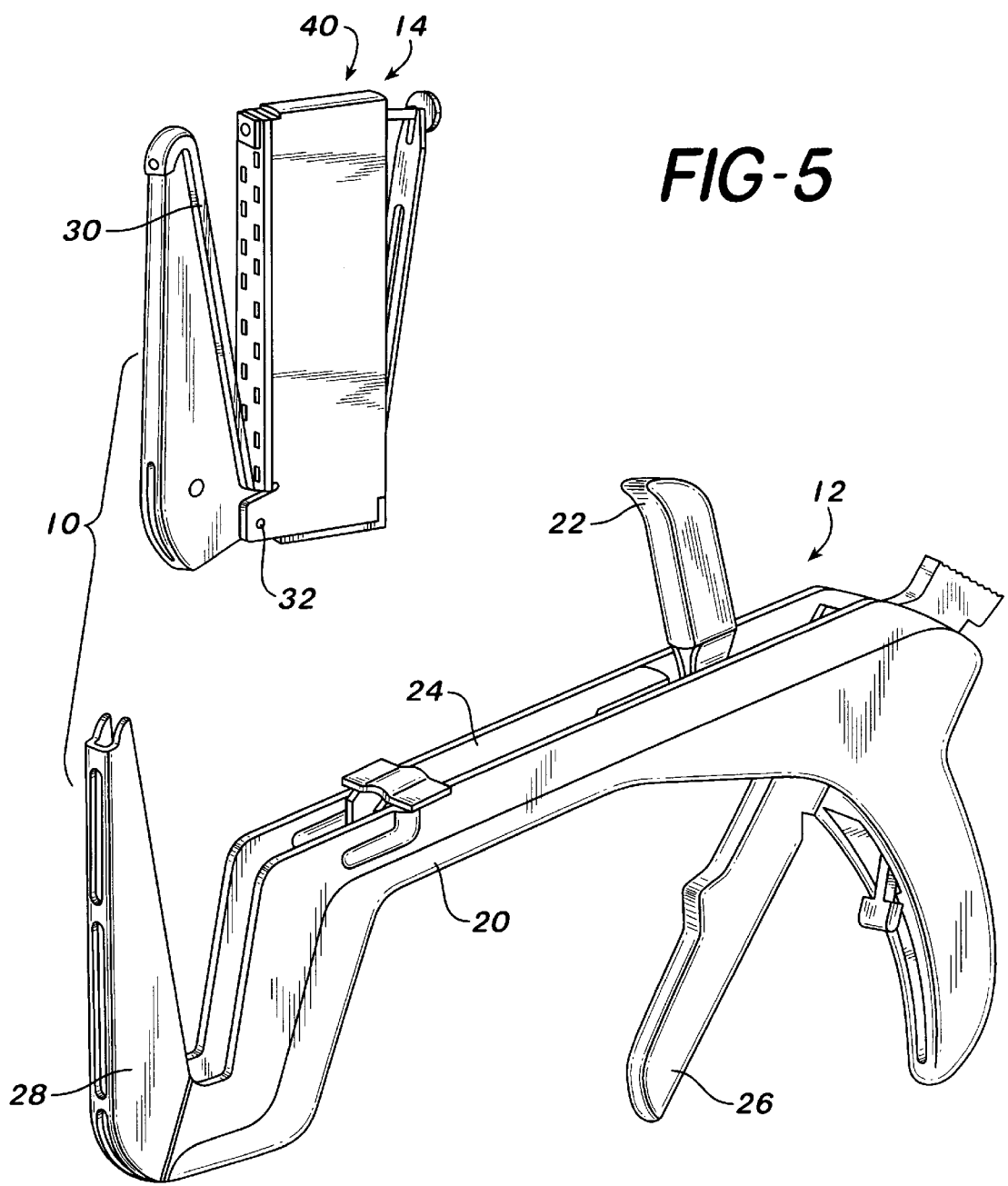
FIG. 5 is a perspective view of an apparatus for applying staples.

"One apparatus for applying staples is shown in FIG. 5 and referred to generally by the reference number 10 consists of two main parts. These are actuator assembly 12 and fastener applying cartridge 14. Actuator assembly 12 may be identical to the corresponding portion of the apparatus shown, co-pending Green U.S. patent application Ser. No. 267,080, filed May 26, 1981. Other actuator assemblies may be readily substituted for the actuator assembly shown. An example of another suitable actuator assembly is shown in co-pending Green U.S. patent application Ser. No. 188,691, filed Sep. 29, 1980. Thus, the particular actuator assembly in FIG. 5 illustrates only one possible environment of the invention and is not necessary to understanding or practicing the invention.

Actuator assembly 12 comprises a frame 20, a clamp actuating mechanism pivoting element 22 and associated reciprocating element 24, and pivoting pusher actuating member 26. Fastener applying cartridge 14 is removably mounted in the distal portion of frame 20 by means of a detent or other similar connection between distal frame leg 28 and fastener retainer support member 30.

Fastener applying cartridge 14 included longitudinal fastener retainer support member 30 and fastener holding assembly 40. Fastener holding assembly 40 is pivotally connected to member 30 by pin 32 adjacent one end of a member 30. Retainer support member 30 contains a plurality of fastener retainer members arranged in two parallel rows. Fastener holding assembly 40 similarly contains a plurality of fastener member arranged in two parallel rows. When fastener holding assembly 40 is pivoted substantially parallel to retainer support member 30, each fastener member is opposite a respective one of retainer members. The fastener members and retainer members in each row are offset from the fastener members and retainer members in the other row to provide a staggered arrangement of finished fasteners in the fastened tissue."

We claim:

1. A surgical device having a latching mechanism comprising:
   a latching member; and a retaining member having at least one aperture adapted to receive and retain said latching member in a locked position, a portion of said latching member and a portion of said retaining member being of contrasting colors so that when the latching member is locked in place by the retaining member that the latching member's presence in the locked position is externally visible.

2. The surgical device of claim 1 wherein the surgical device is composed of a polymeric material.

3. The surgical device of claim 2 wherein the contrasting colors are selected from the group consisting of undyed/green, undyed/violet, undyed/blue, undyed/black, green/black, green/violet, green/blue and blue/black.

4. The surgical device of claim 3 wherein the surgical device has at least one colorant added to the polymeric material to provide the contrasting colors.

5. The surgical device of claim 4 wherein the latching member has a barb with a tip and the retaining member has an aperture and locking surface.

6. The surgical device of claim 5 wherein the polymeric materials in at least a portion of the tip contains colorant.

7. A surgical device having a latching mechanism comprising:
   a latching member having a base with two ends and at least two substantially parallel latches extending perpendicularly from the base each latch having a barb attached to a shank which is connected to the base;
   a retaining member having two apertures adapted to receive and retain said two latches in a locked position;

wherein a portion of said latches and a portion said retaining member being of contrasting colors so that when each latch is locked in place by the retaining member that each latch's presence in the locked position is externally visible.

8. A surgical device having a latching mechanism comprising:

a ligating clip having a latching member and retaining member having proximal and distal ends;

a resilient hinge connecting said latching member and retaining member at their proximal ends;

a latch having a barb connected to a shank attached to the distal end of the latching member;

a retainer having an aperture and a locking surface that are adapted to receive the latch and lock the ligating clip in a closed position in the distal end of the retaining member; and a port located in the distal end of the retaining member to allow visual inspection of the engagement of the latch and retainer;

wherein a portion of said latch member and a portion said retaining member being of contrasting colors so that when the latch member is locked in place by the retaining member that the latch member's presence in the locked position is externally visible.

9. A surgical device comprising:

An apparatus for applying at least one surgical staple having a latching mechanism to join and approximate the edges of a wound in body tissue;

the surgical staple having a latching member and a retaining member, the latching member having a base with two ends and at least two substantially parallel latches extending perpendicularly from the base in substantially the same direction each latch having a barb attached to a shank which is connected to the base adjacent to one end a retaining member having two apertures adapted to receiving and retain said two latches in a locked position; wherein a portion of each of said latches and a portion of said retaining member are of contrasting colors so that when each latch is locked in place by the retaining member each latch's presence in the locked position is externally visible.

10. A surgical device comprising:

an apparatus for applying at least one ligating clip to body tissue;

the ligating clip having a latching member and retaining member having proximal and distal ends, a resilient hinge connecting said latching member and retaining member at their proximal ends, a latch having a barb connected to a shank attached to the distal end of the latching member, a retainer having an aperture and a locking surface that are adapted to receive the latch and lock the ligating clip in a closed position in the distal end of the retaining member and a port located in the distal end of the retaining member to allow visual inspection of the engagement of the latch and retainer; wherein a portion of said latch member and a portion said retaining member being of contrasting colors so that when the latch member is locked in place by the retaining member that the latch member's presence in the locked position is externally visible.

* * * * *

UNITED STATES PATENT AND TRADEMARK OFFICE
CERTIFICATE OF CORRECTION

PATENT NO. : 6,206,897 B1
DATED : March 27, 2001
INVENTOR(S) : Dennis D. Jamiolkowski et al.

It is certified that error appears in the above-identified patent and that said Letters Patent is hereby corrected as shown below:

<u>Column 4,</u>
Line 49, delete "undyed/green".

Signed and Sealed this

Twenty-third Day of May, 2006

JON W. DUDAS
*Director of the United States Patent and Trademark Office*